(12) United States Patent
Brittan et al.

(10) Patent No.: US 7,850,731 B2
(45) Date of Patent: Dec. 14, 2010

(54) ARTICULATING SPINAL IMPLANT

(75) Inventors: Jeff Brittan, Encinitas, CA (US); Colin M. Smith, Dana Point, CA (US)

(73) Assignee: SeaSpine, Inc., Vista, CA (US)

( * ) Notice: Subject to any disclaimer, the term of this patent is extended or adjusted under 35 U.S.C. 154(b) by 0 days.

(21) Appl. No.: 11/543,522

(22) Filed: Oct. 4, 2006

(65) Prior Publication Data
US 2008/0161925 A1   Jul. 3, 2008

(51) Int. Cl.
*A61F 2/44* (2006.01)
(52) U.S. Cl. ................................... 623/17.11
(58) Field of Classification Search ............. 623/16.11, 623/17.11–17.15; 606/246, 249, 71
See application file for complete search history.

(56) References Cited

U.S. PATENT DOCUMENTS

| | | | |
|---|---|---|---|
| 4,401,112 A * | 8/1983 | Rezaian | 606/61 |
| 4,599,086 A | 7/1986 | Doty | |
| 4,759,769 A * | 7/1988 | Hedman et al. | 623/17.13 |
| 6,066,175 A | 5/2000 | Henderson et al. | |
| 6,106,557 A * | 8/2000 | Robioneck et al. | 623/17.15 |
| 6,235,059 B1 * | 5/2001 | Benezech et al. | 623/17.16 |
| 6,409,766 B1 * | 6/2002 | Brett | 623/17.16 |
| 6,432,106 B1 | 8/2002 | Fraser | |
| 6,682,563 B2 | 1/2004 | Scharf | |
| 6,730,127 B2 | 5/2004 | Michelson | |
| 6,837,905 B1 | 1/2005 | Lieberman | |
| 6,962,606 B2 * | 11/2005 | Michelson | 623/17.16 |
| 2003/0105467 A1 * | 6/2003 | Ralph et al. | 606/90 |
| 2004/0049279 A1 * | 3/2004 | Sevrain | 623/17.13 |
| 2005/0101960 A1 * | 5/2005 | Fiere et al. | 606/72 |
| 2006/0224241 A1 * | 10/2006 | Butler et al. | 623/17.15 |

FOREIGN PATENT DOCUMENTS

WO   WO 02/080819 A1   10/2002

* cited by examiner

*Primary Examiner*—Eduardo C Robert
*Assistant Examiner*—Tara R Carter
(74) *Attorney, Agent, or Firm*—McDermott Will &

(57) ABSTRACT

A spinal implant and method of implanting a spinal implant that has a spacer and a plate configured to be fastened to a plurality of vertebral bodies. The plate is coupled to the spacer, with the spacer and the plate being angularly adjustable with respect to each other.

16 Claims, 7 Drawing Sheets

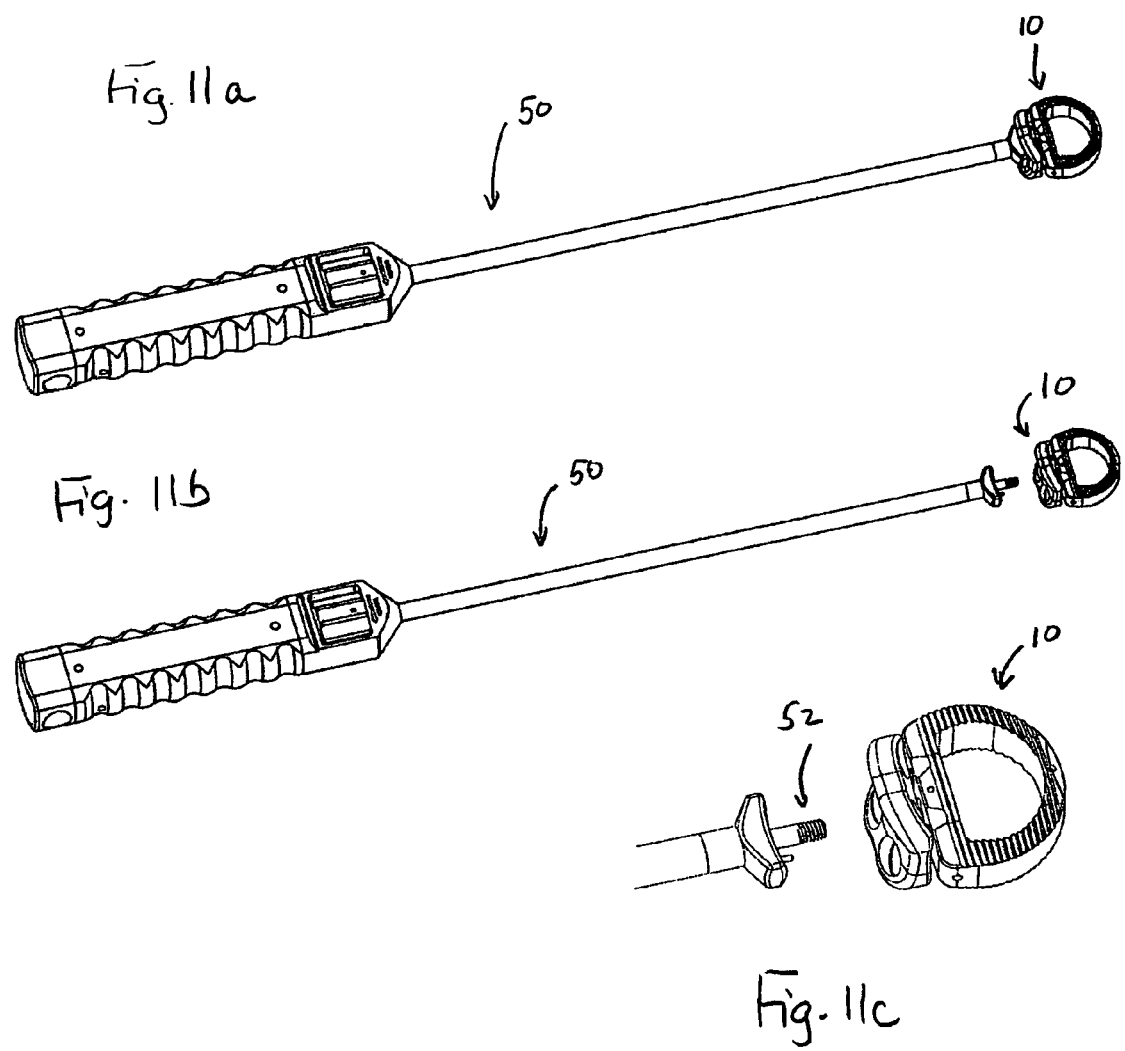

ARTICULATING SPINAL IMPLANT

FIELD

The present invention relates, in general, to artificial prosthetics and, more particularly, to intervertebral spacers.

BACKGROUND

A normal human spine is segmented with seven cervical, twelve thoracic and five lumbar segments. The lumbar portion of the spine resides on the sacrum, which is attached to the pelvis. The pelvis is supported by the hips and leg bones. The bony vertebral bodies of the spine are separated by intervertebral discs, which reside sandwiched between the vertebral bodies and operate as joints allowing known degrees of flexion, extension, lateral bending and axial rotation.

The intervertebral disc primarily serves as a mechanical cushion between adjacent vertebral bodies, and permits controlled motions within vertebral segments of the axial skeleton. The disc is a multi-element system, having three basic components: the nucleus pulposus ("nucleus"), the annulus fibrosus ("annulus") and two vertebral end plates. The end plates are made of thin cartilage overlying a thin layer of hard, cortical bone that attaches to the spongy, richly vascular, cancellous bone of the vertebral body. The plates thereby operate to attach adjacent vertebrae to the disc. In other words, a transitional zone is created by the end plates between the malleable disc and the bony vertebrae.

The annulus of the disc forms the disc perimeter, and is a tough, outer fibrous ring that binds adjacent vertebrae together. The fiber layers of the annulus include fifteen to twenty overlapping plies, which are inserted into the superior and inferior vertebral bodies at roughly a 40 degree angle in both directions. This causes bi-directional torsional resistance, as about half of the angulated fibers will tighten when the vertebrae rotate in either direction.

It is common practice to remove a spinal disc in cases of spinal disc deterioration, disease or spinal injury. The discs sometimes become diseased or damaged such that the intervertebral separation is reduced. Such events cause the height of the disc nucleus to decrease, which in turn causes the annulus to buckle in areas where the laminated plies are loosely bonded. As the overlapping laminated plies of the annulus begin to buckle and separate, either circumferential or radial annular tears may occur. Such disruption to the natural intervertebral separation produces pain, which can be alleviated by removal of the disc and maintenance of the natural separation distance. In cases of chronic back pain resulting from a degenerated or herniated disc, removal of the disc becomes medically necessary.

In some cases, the damaged disc may be replaced with a disc prosthesis intended to duplicate the function of the natural spinal disc. In other cases it is desired to fuse the adjacent vertebrae together after removal of the disc, sometimes referred to as "intervertebral fusion" or "interbody fusion."

In cases of intervertebral fusion, it is known to position a spacer centrally within the space where the spinal disc once resided, or to position multiple spacers within that space. Such practices are characterized by certain disadvantages, including a disruption in the natural curvature of the spine. For example, the vertebrae in the lower "lumbar" region of the spine reside in an arch referred to in the medical field as having a sagittal alignment. The sagittal alignment is compromised when adjacent vertebral bodies that were once angled toward each other on their posterior side become fused in a different, less angled orientation relative to one another.

Surgeons routinely utilize medical device implants such as the interbody spacers discussed above, fixation plates and bone screws in spinal fusion procedures to re-establish disc height and secure vertebral segments. These devices help to stabilize the spine and create an environment in which bone can form to achieve a proper fusion. In order to simplify the implantation procedure and to reduce operating time, implants have been developed that integrate a spacer element and a plate element into a single implant. The use of these integrated devices may offer some advantages over the separate components. However, these device elements are unable to articulate with respect to each other so that the rigid attachment may result in sub-optimal implant positioning. When the spacer element is implanted in the spine, the angle of the associated plate element with respect to the spacer element may not be the best angle to accommodate the patient's anatomy, resulting in a poor fit. Certain designs allow for linear adjustment of the plate position, but the fixed relative angle position of the spacer element and the plate element forms an area of concern.

SUMMARY

There is a need for a spinal implant that is adjustable to accommodate a patient's anatomy.

This and other needs are met by embodiments of the present invention which provide a spinal implant comprising a spacer configured for implantation within a spinal column, and a plate configured to be fastened to a plurality of vertebral bodies. The plate is coupled to the spacer, with the spacer and plate being angularly adjustable with respect to each other.

The earlier stated need and others are also met by embodiments of the present invention which provide a spinal implant comprising a spacer and a fixation plate coupled to the spacer such that the spacer and the fixation plate are angularly adjustable with respect to one another.

The earlier stated need and others are also met by still other embodiments of the present invention which provide a method of implanting a spinal implant having a spacer element and a plate element that are coupled such that the spacer element and the plate element are articulable with respect to each other. The method comprises the steps of inserting the spacer element within a spinal column, articulating the plate element with respect to the spacer element and fastening the plate element to vertebral bodies.

The foregoing and other features, aspects and advantages of the embodiments of the present invention will become more apparent from the following detailed description and accompanying drawings.

BRIEF DESCRIPTION OF THE DRAWINGS

FIG. 11a is a perspective view of a spinal implant according to embodiments of the present invention coupled to an exemplary insertion tool.

FIG. 11b is a perspective view of a spinal implant according to embodiments of the present invention separate from an exemplary insertion tool.

FIG. 11c is a detail of FIG. 11c, showing a tip of the exemplary insertion tool.

FIG. 12b is a front perspective view of the embodiment of FIG. 12a.

FIG. 12c is a side cross-sectional view of the embodiment of FIG. 12a.

FIG. 13b is a front perspective view of the embodiment of FIG. 13a.

DETAILED DESCRIPTION

The embodiments of the present invention address and solve problems related to the implantation of spinal implants into a spine. In particular, the embodiments of the invention overcome limitations of previous spinal implants regarding certain insertion limitations. Embodiments of the invention achieve this, in part, by providing a spinal implant that has a spacer configured for implantation within the spinal column and a plate configured to be fashioned to a plurality of vertebral bodies. The plate is coupled to the spacer, with the spacer and the plate being angularly adjustable with respect to each other. This angular adjustability, or articulation, of the spacer component and a plate element with respect to each other allows the device to better accommodate variations in patient anatomy for a more optimal fit. When a spacer element is implanted in the spine, the adjustable angle of the associated plate element with respect to the spacer element allows the best accommodation of the patient's anatomy.

Figure 1:
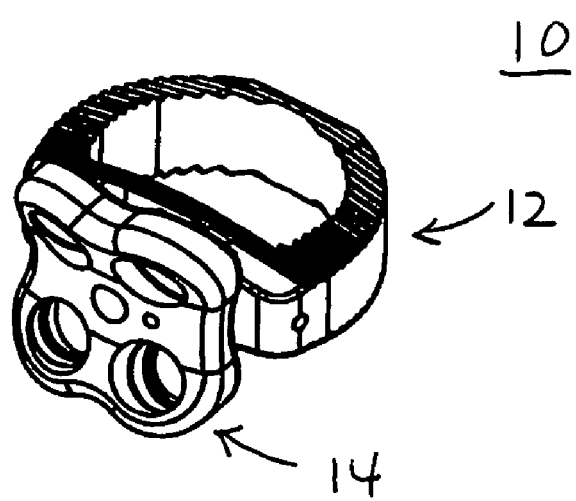
FIG. 1 is a top, perspective view of a spinal implant in accordance with embodiments of the present invention.

FIG. 1 is a perspective view of a spinal implant 10 constructed in accordance with certain embodiments of the present invention. The spinal implant 10 includes a spacer element 12 and a plate element 14 (hereafter "spacer" and "plate," respectively). In FIG. 1, the spacer 12 and plate element 14 are depicted in an assembled state such that the spacer 12 and plate 14 form an integrated spinal implant 10.

Figure 2:
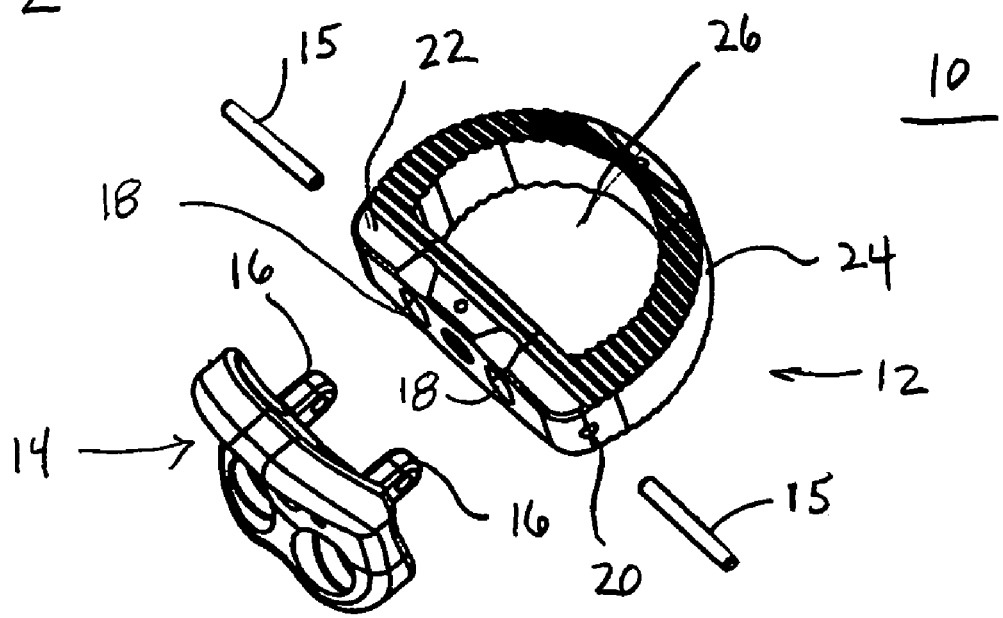
FIG. 2 is an exploded view of the embodiment of the spinal implant of FIG. 1.

FIG. 2 depicts the spinal implant 10 in an exploded view. Spacer 12, which forms a fusion cage in certain embodiments, includes at least one bore 20 into which a hinge pin 15 is inserted. In the embodiment of FIG. 2, two bores 20 are divided with two hinge pins 15 being inserted from opposite ends of a first section or portion 22 of the spacer 12.

The first section 22 of the spacer 12 has at least one recess 18 that receives a hinge post 16 on the plate 14. In the exemplary embodiment of FIG. 2, two recesses 18 are provided to receive respectively two hinge posts 16 of the plate. The hinge pins 15 extend into the hinge posts 16 when assembled.

The spacer 12 includes a second portion 24, which is generally shaped as a semicircle and connects at first and second ends to the first and second ends of the first section or portion 22. A central cavity 26 is defined by the first and second portions 22, 24. The spacer can be considered to form a fusion cage, in certain embodiments.

Figure 3:
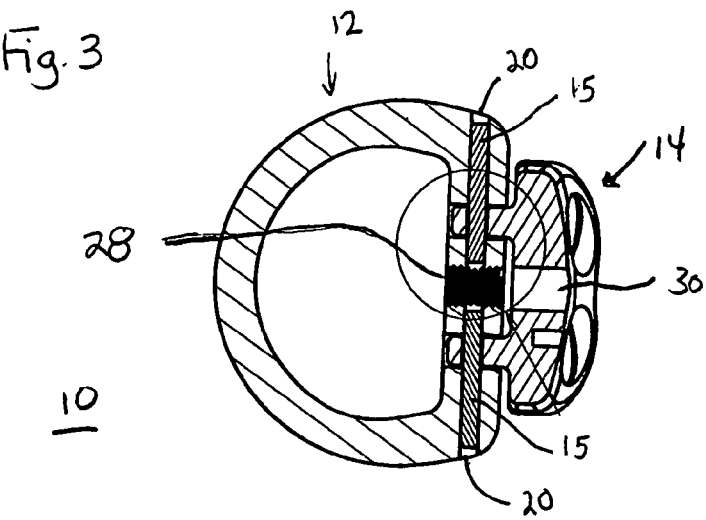
FIG. 3 is a cross-sectional view of the spinal implant of FIG. 1.

FIG. 3 is a cross-sectional view through the spinal implant 10 according to certain embodiments of the present invention. As seen in this embodiment, the bore 20 may be a single bore that extends through the first portion 22, with the two hinge pins 15 being inserted from opposite ends of the first portion 22.

The first portion 22 has a threaded screw receptacle 28 for receiving and temporarily securing a portion of an insertion device (not shown). The plate 14 has a bore 30 through which an insertion tool (not seen in FIG. 3) passes to interact with a threaded screw hole 28. In practice, the insertion tool secures the spinal implant 10 at one end of the insertion tool. The spinal implant 10 is then manipulated by the surgeon into the spine. The insertion tool may then be removed from the threaded screw hole 28. Thereafter, the fasteners (not shown in FIG. 3) fasten the plate 14 to the vertebral body of the spine.

Figure 4A:
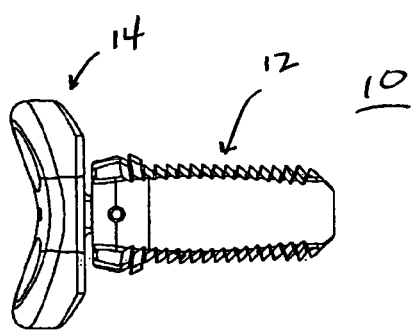
FIGS. 4a-4c depict a side view of the spinal implant of FIG. 1 at various angular positions in accordance with embodiments of the present invention.
Figure 4B:
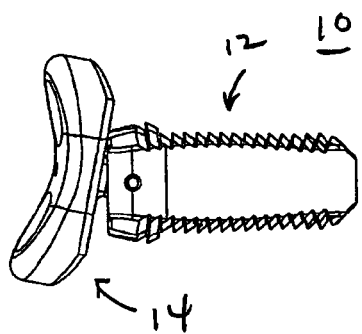
Figure 4C:
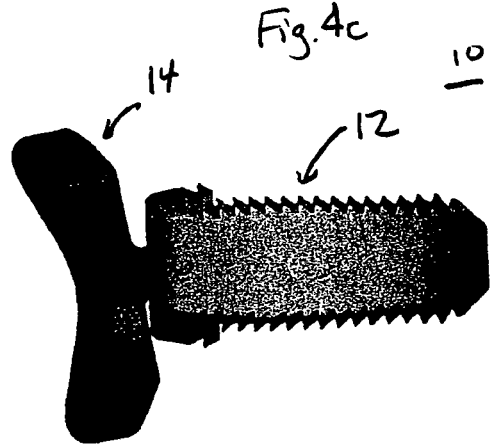

FIGS. 4a-4c depict side views of the spinal implant 10 in accordance with certain embodiments of the present invention. FIG. 4a shows the spinal implant 10 in which the plate 14 is in a nominal position with respect to the spacer 12. In other words, the plate 14 is vertical to a central longitudinal axis through the spacer 12. However, in order to accommodate a patient's anatomy and provide a proper fit, plate 14 and the spacer 12 are angularly adjustable with respect to each other. FIG. 4b and FIG. 4c respectively depict different angular orientations of the plate 14 with respect to the spacer 12. Hence, during the implantation and fixation process, the fixation plate 14 may assume different angular orientations with respect to the spacer 12 to better accommodate the patients anatomy.

Figure 5:
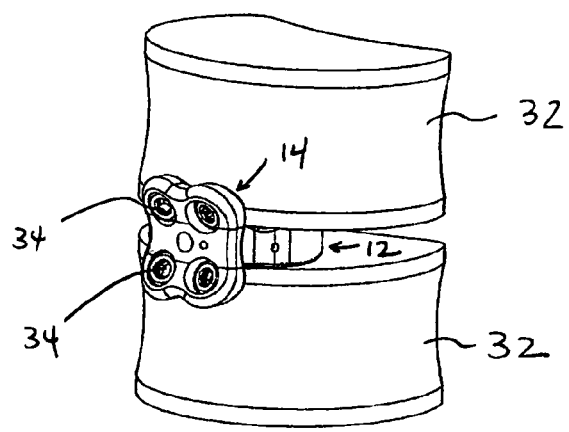
FIG. 5 shows a perspective view of a spinal implant that has been inserted between vertebral bodies and fastened to the vertebral bodies in accordance with embodiments of the methods of the present invention.

An example of an inserted spinal implant 10 is depicted in FIG. 5. The spacer 12 is provided between two vertebral bodies 32. After insertion of the spacer 12, the fixation plate 14 is angularly adjusted to provide the best fit that accommodates the patient's anatomy. Following the angular adjustment, which involves rotating the plate 14 around the hinge pins 15, a set of fasteners 34 fasten the plate 14 to the vertebral body 32.

Figure 6A:
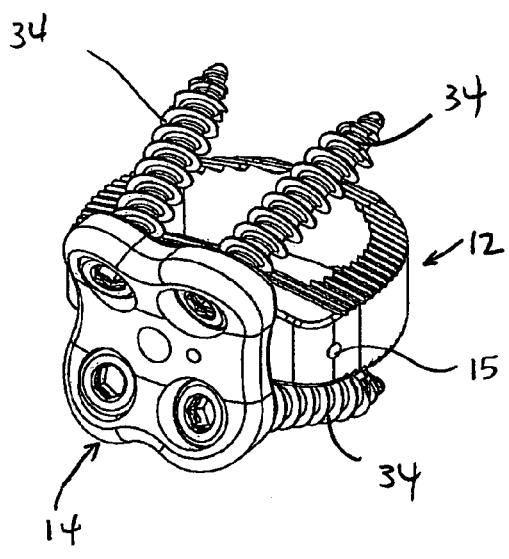
FIGS. 6a-6b show different views of the spinal implant according to embodiments of the present invention with fasteners extending through the plate element.
Figure 6B:
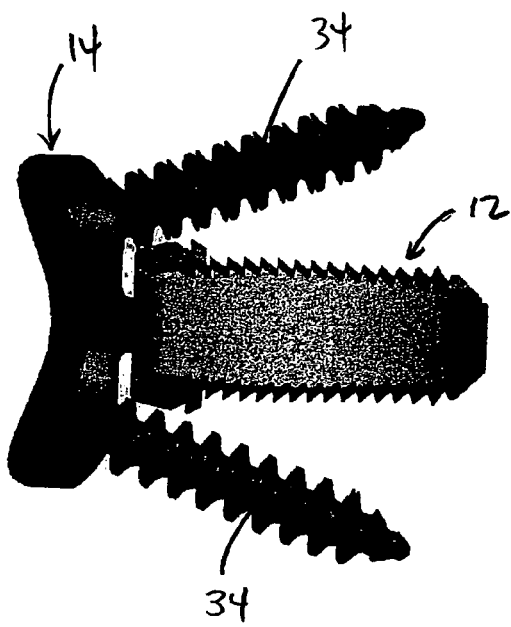

FIG. 6a shows a perspective isolated view of the spinal implant 10 according to embodiments of the present invention, with exemplary fasteners 34 extending through the holes of the plate 14. FIG. 6b is a side view depicting the spinal implant 10 in isolation with the fasteners 34 extending through the holes. In certain embodiments of the invention, the fasteners 34 are titanium screws. However, other types of fasteners may be employed without departing from the scope of the present invention.

Figure 7:
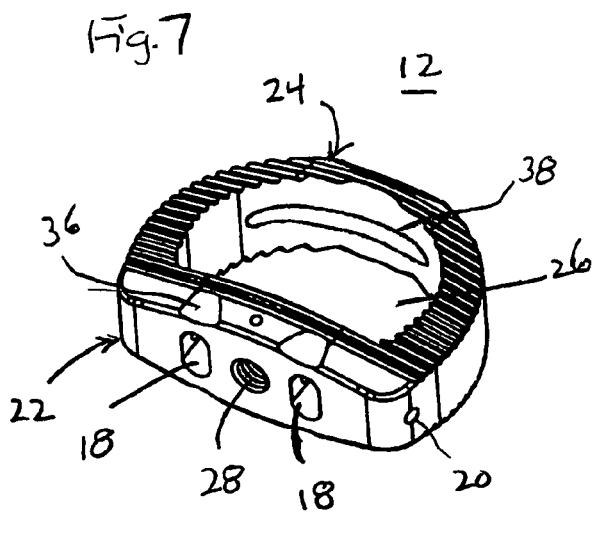
FIG. 7 shows a perspective view of an isolated spacer element constructed in accordance with certain embodiments of the present invention.

FIG. 7 shows an embodiment of the spacer 12 in isolation in accordance with certain embodiments of the present invention. The spacer 12 includes the first portion 22 and the second portion 24, defining the central cavity 26. The bores 20 receive the hinge pins 15 (not shown in FIG. 7). The recesses 18 receive hinge posts 16 (not shown in FIG. 7) of the plate 14. A threaded screw hole 28 is also provided in the first portion 22.

On the top and bottom surfaces of the spacer 12 (only the top surface of which is shown), notches 36 are provided. The notches 36 accommodate passage of the fasteners 34 over the top and bottom surfaces. The notches 36 thereby provide a margin for the fasteners 34 during articulation of the plate 14 with respect to the spacer 12.

The embodiment of FIG. 7 also depicts a slot 38 that is provided in certain embodiments of the invention. Slot 38 is configured to allow compression of the spacer walls between the top and bottom surfaces. The compression that is allowed permits the settling down of the spine and spinal implant 10 during the healing of the bone, which is considered advantageous. In certain other embodiments of the invention, the compression slot 38 is not provided.

Figure 8:
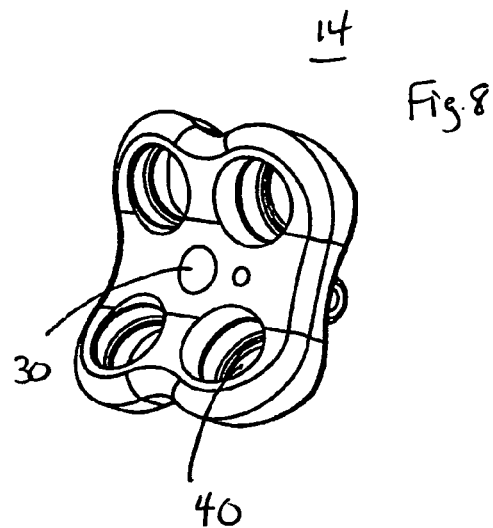
FIG. 8 is a perspective view of an isolated plate element in accordance with certain embodiments of the present invention.
Figure 9:
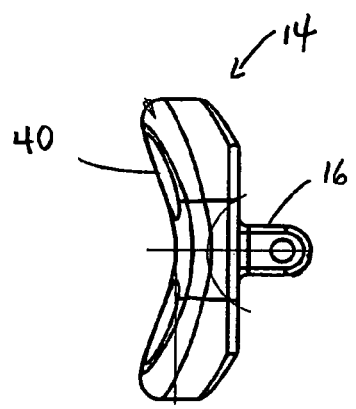
FIG. 9 is a side view of the plate element of FIG. 8.
Figure 10:
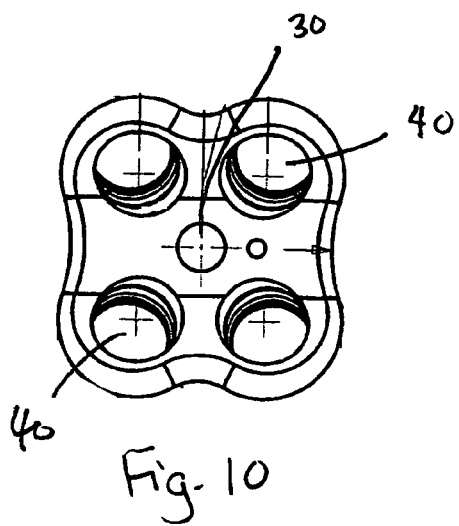
FIG. 10 is a front view of the plate element of FIG. 8.

FIG. 8 is a perspective isolated view of an embodiment of the plate 14. FIG. 9 is a side view of the plate 14 and FIG. 10 is a front view of plate 14. The plate 14 has a plurality of holes 40 that receive the fasteners 34. In the embodiment of FIGS. 8-10, there are four holes 40 for respectively receiving the four fasteners 34. The insertion hole 30 provides access to the threaded screw hole 28 for an insertion tool. In the exemplary embodiment, a pair of hinge posts 16 are provided, although other forms of a hinge may be employed without departing from the scope of the present invention.

An exemplary embodiment of the spinal implant 10 has been described and illustrated in detail above. However, other configurations may be employed without departing from the scope of the present invention. For example, other articulation mechanisms may be employed to provide the relative articulation between the plate 14 and the spacer 12. As examples, a ball and socket mechanism could be employed to provide multiple degrees of freedom and articulation between the plate 14 and the spacer 12.

Figure 13A:
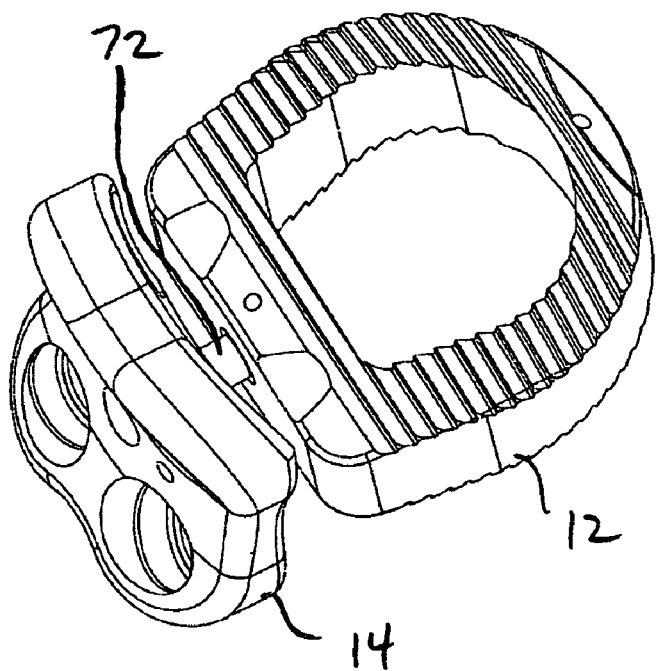
FIG. 13a is a top perspective view of another embodiment of the present invention.
Figure 13B:
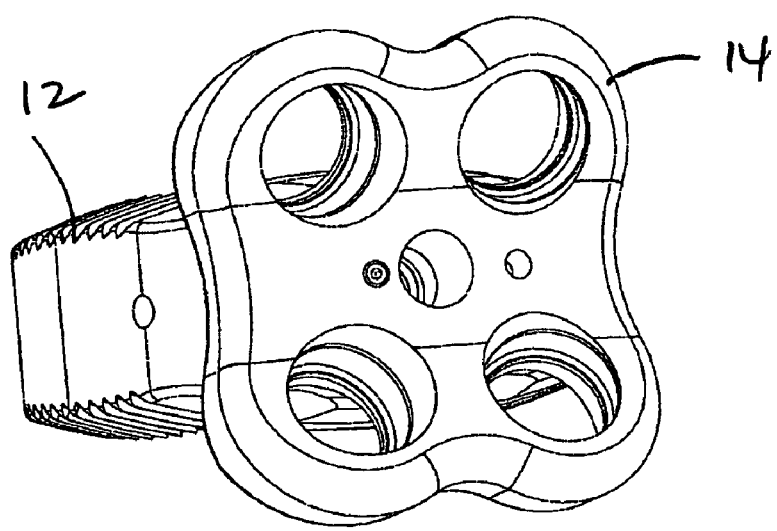

In other exemplary embodiments, such as that shown in FIGS. 13a and 13b, a flexible planar member 72 couples the spacer 12 to the plate 14. Such a flexible member 72 may be made flexible with at least one degree of freedom.

Figure 12A:
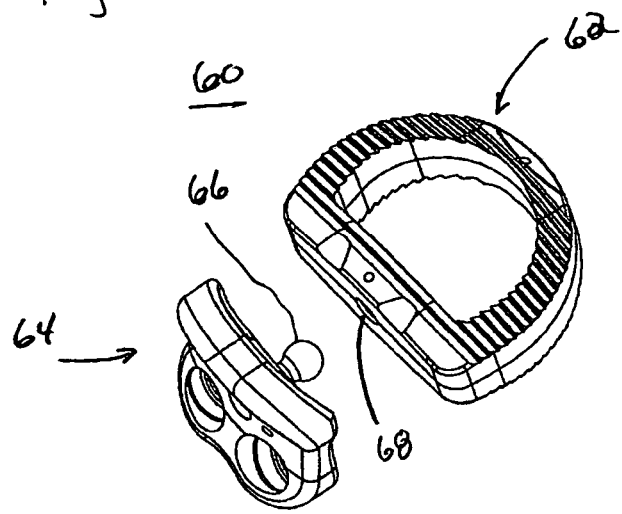
FIG. 12a is an exploded view of a spinal implant constructed in accordance with other embodiments of the present invention.
Figure 12B:
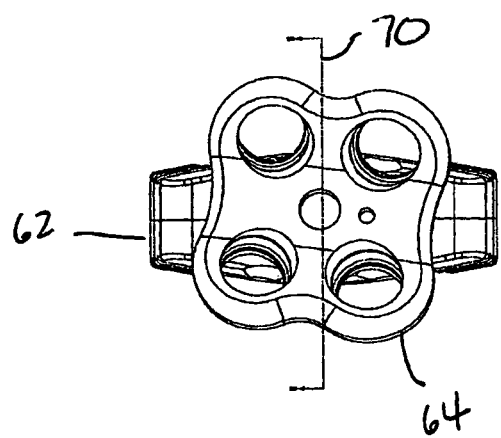
Figure 12C:
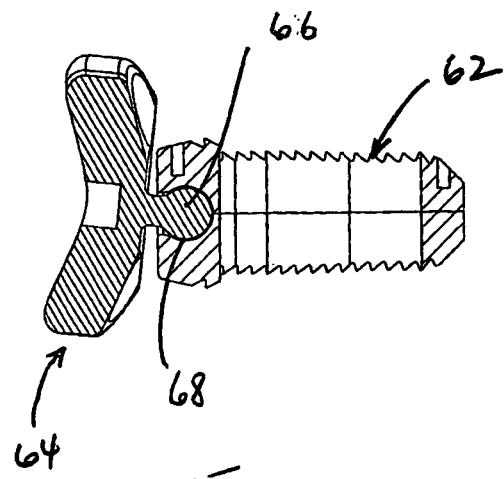

An exemplary embodiment of the present invention which provides multiple degrees of freedom is depicted in FIGS. 12a-12c. The spinal implant 60 of this exemplary embodiment has a spacer element 62 and a plate element 64. The spacer element 62 includes a socket 68 into which a ball 66 of the plate element 64 is insertable. As seen in FIG. 12b, the plate element 64 and the spacer element 62 may be moved with multiple degrees of freedom. In particular, FIG. 12b shows the plate element 64 rotated so as to be off-centered with respect to a vertical axis 70. As well, as seen in the cross-section of FIG. 12c, the plate element 64 and the spacer element 62 may also be angled with respect to one another as in the embodiments of FIGS. 1-10. Other embodiments of the articulation mechanism besides a ball and socket may be employed without departing from the scope of the invention.

FIG. 11a shows a perspective view of a spinal implant 10 coupled to an exemplary insertion tool 50, and FIG. 11b shows the insertion tool 50 separated from the spinal implant 10. FIG. 11c shows the end 52 of the insertion tool 50 according to certain embodiments. The end 52 may be a threaded screw, for example, that passes through bore 30 to interact with the threaded screw hole 28 in the spacer element 12 (see FIG. 3). This configuration is exemplary only, as other configurations for coupling an insertion tool to the spinal implant may be employed without departing from the scope of the invention.

Various shapes and sizes of a spacer 12 and the plate 14 could be employed without departing from the scope of the invention. Similarly, any of a number of different materials may be employed to form the spacer 10 in accordance with embodiments of the present invention. Also, although depicted as freely articulating, certain embodiments of the present invention may provide selective locking of the angle of the plate 14 relative to the spacer element 12. In such embodiments, a relative angle can be set before or after insertion of the spacer 10.

Spinal implant 10 of the present invention provides an integral spacer and fixation plate that may be readily inserted at one time, while accommodating for a patient's individual anatomy to provide a proper fit.

Although embodiments of the present invention have been described and illustrated in detail, it is to be clearly understood that the same is by way of illustration and example only and is not to be taken by way of limitation, the scope of the present invention being limited only by the terms of the appended claims.

What is claimed is:

1. A spinal implant comprising:
   a spacer configured for implantation within a spinal column; and
   a plate configured to be fastened to a plurality of vertebral bodies, the plate having a plane and being coupled to the spacer such that the plate is pivotable about an axis, the spacer and the plane of the plate being angularly adjustable with respect to each other through a continuous range of positions; and
   at least one hinge post extending substantially perpendicularly from the plate;
   wherein the spacer has:
   a first section through which a bore at least partially extends, and at least one recess for receiving the at least one hinge post of the plate; and further comprising a hinge pin extending through the bore, into the recess and into the at least one hinge post in a direction parallel to the plate, the at least one hinge post being rotatable about the hinge pin, whereby rotation of the plate and the at least one hinge post about the hinge pin angularly adjusts the spacer and the plate with respect to each other;
   wherein the plate has at least two of the hinge posts and the first section has at least two recesses for respectively receiving the at least two hinge posts, with two hinge pins extending through the at least two hinge posts respectively.

2. The spinal implant of claim 1, wherein the plate is coupled to the spacer with relative articulation in one degree of freedom.

3. The spinal implant of claim 1, wherein the plate has a plurality of holes configured to receive fasteners for fastening the plate to the vertebral bodies.

4. The spinal implant of claim 1, wherein the spacer comprises spacer walls that define an inner central cavity, the spacer walls having top and bottom surfaces with at least one of the spacer walls including a compression element of the spacer wall between the top and bottom surfaces of the spacer wall.

5. The spinal implant of claim 4, wherein the compression element is a slot.

6. The spinal implant of claim 1, wherein the spacer comprises spacer walls that define an inner central cavity, the spacer walls having top and bottom surfaces and the first section forms one of the spacer walls, and includes notches on the top and bottom surfaces that accommodate passage of the fasteners over the top and bottom surfaces of the first section.

7. The spinal implant of claim 1, wherein the spacer is a fusion cage.

8. The spinal implant of claim 7, wherein the fusion cage has a first portion that is substantially linear and a second portion that is curved and with first and second ends that respectively meet at the first and second ends of the first portion, with a central cavity being defined by the first and second portions.

9. A spinal implant comprising:

a spacer configured for implantation within a spinal column;

a plate configured to be fastened to a plurality of vertebral bodies, the plate being coupled to the spacer such that the plate is pivotable about an axis, the spacer and the plate being angularly adjustable with respect to each other through a continuous range of positions; and at least one hinge post extending substantially perpendicularly from the plate;

wherein the spacer comprises:

a first section through which a bore at least partially extends, and at least one recess for receiving the at least one hinge post of the plate; and further comprising a hinge pin extending through the bore, into the recess and into the at least one hinge post in a direction parallel to the plate, the at least one hinge post being rotatable about the hinge pin, whereby rotation of the plate and the at least one hinge post about the hinge pin angularly adjusts the spacer and the plate with respect to each other; and wherein the plate has at least two of the hinge posts and the first section has at least two recesses for respectively receiving the at least two hinge posts, with two hinge pins extending through the hinge posts respectively.

10. The spinal implant of claim 9, wherein the plate is coupled to the spacer with relative articulation in one degree of freedom.

11. The spinal implant of claim 9, wherein the plate has a plurality of holes configured to receive fasteners for fastening the plate to the vertebral bodies.

12. The spinal implant of claim 9, wherein the spacer comprises spacer walls that define an inner central cavity, the spacer walls having top and bottom surfaces with at least one of the spacer walls including a compression element of the spacer wall between the top and bottom surfaces of the spacer wall.

13. The spinal implant of claim 12, wherein the compression element is a slot.

14. The spinal implant of claim 9, wherein the spacer comprises spacer walls that define an inner central cavity, the spacer walls having top and bottom surfaces and the first section forms one of the spacer walls, and includes notches on the top and bottom surfaces that accommodate passage of the fasteners over the top and bottom surfaces of the first section.

15. The spinal implant of claim 9, wherein the spacer is a fusion cage.

16. The spinal implant of claim 15, wherein the fusion cage has a first portion that is substantially linear and a second portion that is curved and with first and second ends that respectively meet at the first and second ends of the first portion, with a central cavity being defined by the first and second portions.

* * * * *